US012605347B2

(12) United States Patent
Allegrini et al.

(10) Patent No.: US 12,605,347 B2
(45) Date of Patent: Apr. 21, 2026

(54) SOLID DISPERSION OF URSOLIC ACID AND POTASSIUM SALT

(71) Applicant: Indena S.P.A., Milan (IT)

(72) Inventors: Pietro Allegrini, Milan (IT); Daniele Ciceri, Milan (IT); Lorenzo Menna, Milan (IT)

(73) Assignee: Indena S.P.A., Milan (IT)

( * ) Notice: Subject to any disclaimer, the term of this patent is extended or adjusted under 35 U.S.C. 154(b) by 1007 days.

(21) Appl. No.: 17/755,720

(22) PCT Filed: Oct. 30, 2020

(86) PCT No.: PCT/EP2020/080548
§ 371 (c)(1),
(2) Date: May 6, 2022

(87) PCT Pub. No.: WO2021/089433
PCT Pub. Date: May 14, 2021

(65) Prior Publication Data

US 2022/0387361 A1 Dec. 8, 2022

(30) Foreign Application Priority Data

Nov. 6, 2019 (IT) ........................ 102019000020492

(51) Int. Cl.
*A61K 31/19* (2006.01)
*A61K 9/16* (2006.01)

(52) U.S. Cl.
CPC ............ *A61K 31/19* (2013.01); *A61K 9/1611* (2013.01); *A61K 9/1617* (2013.01); *A61K 9/1652* (2013.01)

(58) Field of Classification Search
CPC ........ C07J 63/00; A61K 31/19; A61K 9/1617; A61K 9/1611; A61K 9/1652
See application file for complete search history.

(56) References Cited

FOREIGN PATENT DOCUMENTS

| | | | | |
|---|---|---|---|---|
| CN | 101095684 | A | | 1/2008 |
| CN | 101716154 | A | * | 6/2010 |
| JP | 2004331593 | A | * | 11/2004 |

OTHER PUBLICATIONS

Wang et al. Pharmaceutical Development and Technology 2020, 25 (1), 68-75, published online Oct. 1, 2019.*
Biswas et al. Drug development and industrial pharmacy 2019, 45 (6), 946-958, published online Mar. 5, 2019.*
Search Report and Written Opinion of PCT/EP2020/080548 of Mar. 10, 2021.
Zhou X. J. et al., "Preparation and body distribution of freeze-dried powder of ursolic acid phospholipid nanoparticles", Drug Development and Industrial Pharmacy, vol. 35, No. 3, Mar. 1, 2009, pp. 305-310.

* cited by examiner

*Primary Examiner* — Irina Neagu
(74) *Attorney, Agent, or Firm* — Silvia Salvadori, P.C.; Silvia Salvadori

(57) ABSTRACT

The present invention relates to solid dispersions comprising a salt of ursolic acid with an alkali metal and a phospholipid and to oral dosage formulations containing them. The invention also relates to processes for preparing the solid dispersions and to the use of the solid dispersions and formulations for the prevention and/or treatment of a variety of pathological conditions in which hepatoprotective, antioxidant, anti-inflammatory, antiviral and cytotoxic activities are desired.

12 Claims, No Drawings

SOLID DISPERSION OF URSOLIC ACID AND POTASSIUM SALT

This application is a U.S. national stage of PCT/EP2020/080548 filed on 30 Oct. 2020, which claims priority to and the benefit of Italian Patent Application No. 1020190000120492 filed on 6 Nov. 2019, the contents of which are incorporated herein by reference in their entireties.

BACKGROUND OF THE INVENTION

Ursolic acid (3β-hydroxy-urs-12-en-28-oic acid), having formula (1):

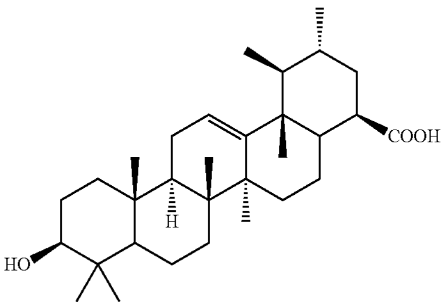

(1)

is a naturally occurring pentacyclic triterpene acid that is widely present in many plants and also in many fruits and herbs used in daily life, for example apples, bilberries, cranberries, basil, rosemary, oregano and thyme, to name but a few. The peels of fruits, in particular apple peels, may also contain large amounts of ursolic acid. Ursolic acid is endowed with a number of biological effects, such as hepatoprotective, antioxidant, anti-inflammatory, antiviral and cytotoxic activities and, due to its low toxicity, it is a promising candidate for the nutraceutical market. However, ursolic acid is poorly soluble in aqueous media, thus it is scarcely bioavailable through oral administration; moreover, ursolic acid has low membrane permeability. For such reasons, ursolic acid is classified as a class IV molecule according to the biopharmaceutical classification system (BCS). The BCS, developed by Amidon et al. (Pharm Res. 1995 March; 12(3):413-20), is based on the finding that drug dissolution in the gastrointestinal fluids and permeability through the gastrointestinal membrane are the fundamental parameters that control the rate and extent of drug absorption. According to the BCS, molecules can be classified into four categories, depending on their solubility and permeability properties: high solubility-high permeability (class I); low solubility-high permeability (class II); high solubility-low permeability (class III); and low solubility-low permeability (class IV). A number of formulation strategies have been developed to improve the bioavailability of active principles belonging to the four different classes. Theoretically, an ideal approach to improve the bioavailability of a class IV molecule would be to modify its structure in order to obtain the required physicochemical properties. However, finding a more bioavailable ursolic acid derivative would not only be challenging, time consuming and costly, but also any such derivative could not be used in the nutraceutical field.

The use of polymeric nanoparticulate systems to improve bioavailability, when successful, would be suitable only for medicinal products and not for products intended for the nutraceutical market (Current medicinal chemistry 2017, 24, 1-10).

This disadvantage also accompanies other formulation approaches present in the known art, such as the nanoparticles of ursolic acid described by Zhou et al (Drug Development and Industrial Pharmacy 2009 35 3 305); said preparation, containing ursolic acid, soy phospholipids and poloxamer 188 and administrable by injection, is difficult to use in the nutraceutical field, where formulations that can be administered orally are preferred.

Since thermodynamic solubility also depends on crystal size, according to Wu W. et al. (Journal of Solution Chemistry 27(6):521-531, 1998), the use of nanocrystals allowed an increase of solubility of 2.56 times compared to coarse ursolic acid (J. Pi, et al. Current drug delivery (2016), 13(8), 1358-1366). However, nanocrystals are difficult to formulate because of their poor flowability.

On the contrary, the phospholipid complexes of ursolic acid and lecithins, disclosed in Chinese patent application 101095684, can be formulated in oral dosages such as capsules, tablets, etc.; however, although the complexation with lecithins leads to an increase in bioavailability, the ratio of acid to phospholipids is not less than 1:4. This ratio implies a low amount of active in the complex, resulting in the need to prepare pharmaceutical or nutraceutical formulations at high dosage or to be administered in repeated doses.

Therefore, the need is still felt of a simple and industrially sustainable way to increase the solubility of ursolic acid.

DESCRIPTION OF THE INVENTION

The Applicant has now found out that salts of ursolic acid with alkali metals, for example with potassium, can be dispersed in phospholipids to form solid dispersions and that such dispersions [solid dispersions SD] are much more soluble in gastric fluids compared to free ursolic acid salts, free ursolic acid and also compared to solid dispersions of ursolic acid with phospholipids, but lacking alkali metals. This is quite surprising, because, in theory, the solubility of hydrophilic or amphiphilic molecules, like ursolic acid salts with alkali metals, would not benefit from being dispersed in a phospholipid matrix.

Therefore, in one aspect, the present invention relates to a solid dispersion [solid dispersion SD] comprising:

a) a salt of ursolic acid with an alkali metal, for example with sodium and potassium, more preferably with potassium and b) a phospholipid.

According to a preferred aspect, solid dispersions SD comprise one or more pharmaceutical or nutraceutical excipients suitable for modifying the rheological properties [excipient (E)], allowing the manufacture of oral pharmaceutical or nutraceutical formulations [formulations (F)].

Examples of excipients (E) include, but are not limited to:

- soluble and insoluble diluents, such as cellulose, preferably microcrystalline cellulose, cellulose ethers, calcium phosphate, calcium carbonate, mannitol, maltodextrins, isomalt and combinations thereof;
- lubricants and/or glidants, such as silica, talc, stearic acid, magnesium stearate and combinations thereof;
- surfactants, such as sucrose esters, polysorbates, polyoxyethylenated castor oil derivatives, D-α-tocopheryl-polyethylene glycol succinate (Vitamin E TPGS) and combinations thereof.

The above and further excipients are disclosed, for example, in Remington: "The Science and Practice of Pharmacy", 22nd edition, Pharmaceutical Press, 2013 (the disclosure of which is incorporated by reference herein in its entirety).

In an exemplary embodiment, a solid dispersion SD consists essentially of:

a) a salt of ursolic acid with an alkali metal, preferably with sodium and potassium, more preferably with potassium;
b) a phospholipid;
c) cellulose or a cellulose ether or a combination thereof; and
d) silica.

In embodiments herein that "consist essentially" of the recited ingredients, such solid dispersions SD contain the recited components and those that do not materially affect the basic and novel characteristics of the claimed solid dispersions SD. Components that do not materially affect the basic and novel characteristics of the claimed solid dispersions are those that do not impair the solubility of the solid dispersions SD in gastric fluids compared to free ursolic acid salts, free ursolic acid and also compared to solid dispersions of ursolic acid with phospholipids, but lacking alkali metals. Examples of components that would not materially affect the basic and novel characteristics of the claimed solid dispersions SD, and thus could be included in solid dispersions SD that consist essentially of the recited components, include various excipients, such as soluble and insoluble diluents, such as cellulose, preferably microcrystalline cellulose, cellulose ethers, calcium phosphate, calcium carbonate, mannitol, maltodextrins, isomalt and combinations thereof; lubricants and/or glidants, such as silica, talc, stearic acid, magnesium stearate and combinations thereof; surfactants, such as sucrose esters, polysorbates, polyoxyethylenated castor oil derivatives, D-α-tocopheryl-polyethylene glycol succinate (Vitamin E TPGS) and combinations thereof.

In a preferred embodiment, a solid dispersion SD consists of:

e) a salt of ursolic acid with an alkali metal, preferably with sodium and potassium, more preferably with potassium;
f) a phospholipid;
g) cellulose or a cellulose ether or a combination thereof;
h) silica.

Even more preferably, a dispersion SD consists of ursolic acid potassium salt, a phospholipid, cellulose and silica.

In the present description, the expression "ursolic acid salt" is intended to denote a salt of ursolic acid with an alkali metal and is intended to comprise the preferred and more preferred salts identified above.

In general, when terms are used herein in their broadest scope, each narrower scope (preferred definitions) are included, unless stated otherwise.

The term "phospholipid" identifies a substance selected from one or more lecithins obtained from soy, sunflower, egg or any other plant or animal source and which comprise phosphatidyl choline, phosphatidyl serine, phosphatidyl ethanolamine and mixtures thereof, in which the acyl groups may the same or different and can be derived from palmitic, stearic, oleic, linoleic or linolenic acids. According to a preferred embodiment, the phospholipid is soy lecithin. According to another preferred aspect, the phospholipid is sunflower lecithin.

The term "solid dispersion SD" or "SD" or "solid dispersion" as used herein indicates that the formulation contains a salt of ursolic acid with an alkali metal, in an inert carrier (phospholipid) in a solid state prepared by solvent method. The SD is deposited over the surface of microcrystalline cellulose or a cellulose ether or a combination thereof.

The solid dispersions described herein suitably do not contain any aqueous phase in which the solid state is suspended or dispersed, and specifically exclude liposomes, oil-in-water emulsions and other aqueous dispersions.

Solid dispersions SD suitably comprise the ursolic acid salt and the phospholipid in a weight ratio from 0.2:1 to 3:1, including from 0.3:1 to 3:1, from 0.4: to 2:1, preferably from 0.5:1 to 2:1, or from 0.5:1 to 1:1, or 1:1. Ratios denoting reciprocal amounts of solid ingredients are expressed as weight ratios, unless stated otherwise. When ranges are indicated, range ends are included. In exemplary embodiments, the amount of ursolic acid salt in the solid dispersions SD is in a weight percentage from [j1] 16% to 75% w/w, including from 22% to 75%, from 28% to 66%, preferably from 33% to 66%, or from 33% to 50%, or 50%.

Solid dispersions SD can be prepared through a process [process (P1)] which comprises:

a-1) mixing an ursolic acid salt and a phospholipid in an alcohol, preferably a $C_1$-$C_3$ aliphatic alcohol, more preferably ethanol, to provide a suspension;
b-1) heating the suspension obtained in step a-1) under reflux for a time ranging from
5 minutes to 5 hours, preferably from 1 to 3 hours;
c-1) removing the solvent to provide a solid dispersion SD.

In step a-1), the ursolic acid salt and the phospholipids are mixed in a weight ratio from 0.2:1 to 3:1, preferably from 0.5:1 to 2:1. The alcohol is used in an amount ranging from 10 to 20 volumes with respect to the amount of ursolic acid salt. The selected ursolic acid salt can optionally be prepared in situ by suspending ursolic acid in the selected alcohol and adding a metal hydroxide. In particular, ursolic acid potassium salt is prepared by suspending ursolic acid in ethanol, followed by the addition of potassium hydroxide.

In step b-1), heating is carried out at the reflux temperature of the selected alcohol.

In step c-1), most of the alcohol is typically removed by evaporation under reduced pressure to provide a solid residue, which is a SD with residual alcohol then complete removal of the alcohol is carried out by heating the residue under vacuum at a temperature ranging from 30° C. to and 70° C., preferably at 60° C. Complete removal means that the amount of alcohol detected by GC (gas chromatography) analysis is lower than the ICH limits (i.e. 5000 ppm for ethanol).

The obtained powder (dried SD) is then ground to obtain the desired particle size, which typically ranges from 10 μm to 300 μm.

Solid dispersions SD further comprising one or more excipients (E) can be prepared either by dry mixing the selected excipients to the dispersions obtained at the end of step c-1) and then grinding to the desired particle size or through a process [process (P2)] which comprises adding one more excipients (E) during step a-1) as described above and, optionally, also at the end of step c-1).

Therefore, process (P2) comprises the following steps:

a-2) mixing an ursolic acid salt, a phospholipid and an excipient (E) in an alcohol, preferably a $C_1$-$C_3$ aliphatic alcohol, more preferably ethanol, to provide a suspension;
b-2) heating the suspension obtained in step a-2) under reflux for a time ranging from
5 minutes to 5 hours, preferably from 1 to 3 hours;

c-2) removing of the solvent to obtain a solid, optionally adding a further excipient (E) and grinding to provide a solid dispersions SD.

In step a2), ursolic acid salt and the phospholipids are mixed in a weight ratio from 0.2:1 to 3:1, preferably from 0.5:1 to 2:1. The solvent is used in an amount ranging from 10 to 30 volumes with respect to the amount of ursolic acid. Similarly to process (P1), also in process (P2) the selected ursolic acid salt can optionally be prepared in situ by suspending ursolic acid in the selected alcohol and adding a metal hydroxide. In particular, ursolic acid potassium salt is prepared by suspending ursolic acid in ethanol, followed by the addition of potassium hydroxide.

In step a-2), excipient (E) is used in a weight ratio from 0.1:1 to 1:2, preferably of 0.5:1 with respect to the ursolic acid salt.

In step b-2), heating is carried out at the reflux temperature of the selected alcohol.

In step c-2), most of the alcohol is typically removed by evaporation under reduced pressure to provide a solid residue, which is submitted to heating under vacuum at a temperature ranging from 30° C. to 70° C., preferably at 60° C., to completely remove any residual alcohol. The resulting solid residue can then be mixed with a further excipient (E) to provide a solid dispersion SD with the desired particle size, which typically ranges 10 μm to 300 μm. Any excipient (E) added after step c-2) is used in an amount ranging from 0.01:1 to 0.1:1 with respect to the solid residue obtained after complete solvent removal. Thus, the overall weight ratio of excipient (E) with respect to the ursolic acid salt can range from 0.5:1 to 2:1.

In a process (P2) for the preparation of preferred solid dispersions SD consisting of an alkali metal salt of ursolic acid, a phospholipid, microcrystalline cellulose and silica, microcrystalline cellulose is added in step a-2), while silica is added at the end of step c-2) before grinding.

As anticipated above, experiments carried out by the Applicant have demonstrated that the solid dispersions SD according to the present invention are much more soluble in simulated gastric fluids with respect to free ursolic acid salts, free ursolic acid and also compared to solid dispersions of ursolic acid with phospholipids, but that lack alkali metals. Indeed, simulation of gastrointestinal conditions is essential to adequately predict the in vivo behavior of products and to reduce the size and number of human studies required to identify a drug product with appropriate performance in both fed and fasted state (Klein, S.; AAPS Journal 2010, 12, 3, 397-406). The Applicant used three different simulated gastric fluids at three different pH values (pH 1.6, 6.5 and 5.0) to simulate fasted state in the stomach, fasted state in the intestine and fed state in the intestine and observed that:

the solubility of solid dispersions SD at pH 1.6 was from 0.5 to 0.3 mg/ml and about 6 to 13 fold higher than the solubility of a corresponding solid dispersion of ursolic acid in a phospholipid;

the solubility of solid dispersions SD at pH 6.5 was 1.1 to 1.2 mg/ml and about 2.5 to 2.8 fold higher than the solubility of the corresponding solid dispersion of ursolic acid in a phospholipid;

the solubility of solid dispersions SD at pH 5.0 was from 0.8 to 1.1 mg/ml and from 2 to 2.5 fold higher than the solubility of a corresponding solid dispersion of ursolic acid in a phospholipid.

In view of the high solubility in simulated gastrointestinal fluids, solid dispersions SD, can be advantageously used to prepare oral dosage formulations [formulations (F)]. Thus, formulations (F) comprising solid dispersions SD and further ingredients of pharmaceutical or nutraceutical grade are a further aspect of the present invention. Examples of formulations (F) include, without limitation, chewable tablets, capsules, soft gelatin capsules, hard gelatin capsules, lozenges, chewable lozenges, health bars, confections, animal feeds, cereals, cereal coatings, and combination thereof. Formulations (F) can be prepared through methods and with ingredients known in the art, which as skilled person will be able to select on a case-by-case basis according to specific needs. Non-limiting examples of such ingredients include, but are not limited to, disintegrants, lubricants, binders, coating agents, colorants, absorption promoters, solubilizing agents, stabilizers, flavor sweeteners, antiseptics, preservatives, antioxidants and the like.

The solid dispersions SD and formulations (F) according to the present invention can be used for the prevention and/or treatment of Alzheimer's disease, Parkinson's disease, motor neuron disease, acute kidney injury, kidney disease, nonalcoholic fatty liver disease, type 2 diabetes, cardiovascular disease, muscular dystrophy, neuromuscular disorders, sarcopenia and muscle atrophy disorders.

The invention is disclosed in greater detail in a non-limiting manner in the following experimental section.

EXPERIMENTAL SECTION

Materials

Ursolic acid is commercially available from Sigma Aldrich.

Microcrystalline cellulose (Avicel®) is available from DuPont.

Silica (Syloid®) is available from Grace.

Simulating gastric fluids FaSSGF pH 1.6, FaSSIF pH 6.5 and FaSSIF pH 5.5 are commercially available from BioRelevant.

Ursolic acid potassium was prepared from ursolic acid by standard procedures.

Methods

Analysis of the solid dispersions and the measure of the solubility in simulated gastrointestinal fluids were performed by HPLC with the instrument and conditions reported below.

Column

Stationary phase: Symmetry C18.

Size: 1=250 mm ; I.D.=4.6 mm, particle size 5 μm.

Manufacturer: Waters; P/N: WAT054275.

Mobile phase

Solvent A: formic acid 0.01% in water (V/V)

Solvent B: formic acid 0.01% in acetonitrile (V/V)

Solvent C: methanol

Linear gradient

| Time (min) | Solvent A (%) | Solvent B (%) | Solvent C (%) |
|---|---|---|---|
| 0.0 | 10 | 70 | 20 |
| 23.0 | 2 | 78 | 20 |
| 26.0 | 2 | 78 | 20 |
| 28.0 | 10 | 70 | 20 |
| 32.0 | 10 | 70 | 20 |

Analysis conditions

Flow rate: 1.0 ml/minute

Detection: 205 nm

Injection volume: 10 μm

Column temperature: 15° C.
Autosampler temperature: 20° C.
Run time: 32 minutes

PREPARATIVE EXAMPLES

Example 1 (According to the Invention)—Solid Dispersion of Ursolic Acid Potassium Salt in Phospholipids (In Situ Preparation of Ursolic Acid Potassium Salt)

Ursolic acid (2.5 g, 90% purity, 4.92 mmol) was suspended in ethanol (30 ml) and the resulting suspension was added first with a 4% w/w solution of potassium hydroxide in ethanol (1.16 eq), then with sunflower lecithin (5 g) and heated under reflux for 15 minutes. The solvent was evaporated to dryness under reduced pressure to provide a solid residue that was dried under vacuum at 60° C. and then ground. 7.5 g of dry solid was obtained.

Example 2 (According to the Invention)—Solid Dispersion of Ursolic Acid Potassium Salt in Phospholipids, Microcrystalline Cellulose and Silica (In Situ Preparation of Ursolic Acid Potassium Salt)

Ursolic acid (2.5 g, 90% purity, 4.92 mmol) was suspended in ethanol (30 ml) and the resulting suspension was added first with a 4% w/w solution of potassium hydroxide in ethanol (1.16 eq), then with sunflower lecithin (3.75 g) and microcrystalline cellulose (1.25 g). The suspension was heated under reflux for 15 minutes, then the solvent was evaporated to dryness under reduced pressure to provide a solid residue which was dried under vacuum at 60° C. and then ground in the presence of silica (75 mg). Yield: 7.5 g of title product.

Example 3 (According to the Invention)—Solid Dispersion of Ursolic Acid Potassium Salt in Phospholipids, Microcrystalline Cellulose and Silica Ursolic acid potassium salt (6.5 g, assay 77%), sunflower lecithin (7.5 g) and microcrystalline cellulose (2.5 g) were suspended in ethanol and heated at reflux for 15 minutes. The solvent was evaporated to dryness under reduced pressure to provide a solid residue which was dried under vacuum at 60° C. and then ground in the presence of silica (0.16 g) Obtained 15 g of title product.

Example 4(Comparative)—Solid Dispersion of Ursolic Acid with Phospholipids (Lacking Alkali Metal)

Ursolic acid (0.5 g, assay 94%) and sunflower lecithin (1.0 g) were suspended in ethanol and heated at reflux for 60 minutes. The solvent was evaporated to dryness under reduced pressure to provide a solid residue which was dried under vacuum at 60° C. and then ground. Obtained 1.5 g of title product.

DISSOLUTION TESTS

Test 1—Dissolution of the Solid Dispersion of Ursolic Acid Potassium Salt with Phospholipids The solid dispersion of ursolic acid potassium salt with phospholipids (300 mg) according to example 1 was suspended in the simulated gastrointestinal fluid of choice (20 mL) and stirred for 2 hours at 25° C. Stirring was stopped and any undissolved solid was let to decant. The supernatant was filtered through a hydrophilic 0.2 μm PTFA filter and analyzed for the content of ursolic acid.

Test 5—Dissolution of the Solid Dispersion of Ursolic Acid Potassium Salt Formulated with Microcrystalline Cellulose and Silica The same procedure as Test 1 was followed, using 300 mg of the solid dispersion of ursolic acid potassium salt with phospholipids formulated with microcrystalline cellulose and silica according to example 3 instead of the dispersion of example 1.

Test 2(Comparative)—Dissolution of Ursolic Acid

The same procedure as Test 1 was followed, using 100 mg of ursolic acid instead of the dispersion of example 1.

Test 3(Comparative)—Dissolution of Ursolic Acid Potassium Salt

The same procedure as Test 1 was followed, using 100 mg ursolic acid potassium salt instead of the dispersion of example 1.

Test 4(Comparative)—Dissolution of a Solid Dispersion of Ursolic Acid with Phospholipids The same procedure as Test 1 was followed, using 300 mg of the solid dispersion of ursolic acid with phospholipids instead of the dispersion of example 1.

The test results are reported in the table 1 below. As shown, solid dispersions SD prepared using a salt of ursolic acid with an alkali metal and a phospholipid provided the highest dissolution of ursolic acid, compared with alkali metal alone, as well as a solid dispersion SD that lacked alkali metal.

TABLE 1

| | FaSSGF pH = 1.6 | | | | |
|---|---|---|---|---|---|
| | Test 1 (solid dispersion of ursolic acid potassium salt with phospholipids) | Test 2 (solid dispersion of ursolic acid potassium salt of example 3 | Comparative test 3 (ursolic acid) | Comparative test 4 (ursolic acid potassium salt) | Comparative test 5 (solid dispersion of ursolic acid with phospholipids) |

TABLE 1-continued

| | | | | | |
|---|---|---|---|---|---|
| Ursolic acid in solution (mg/ml) | 0.546 | 0.295 | <LOD* | <LOD* | 0.043 |

| | FaSSIF pH = 6.5 | | | | |
|---|---|---|---|---|---|
| | Test 1 (solid dispersion of ursolic acid potassium salt with phospholipids) | Test 2 (solid dispersion of ursolic acid potassium salt of example 3 | Comparative test 3 (ursolic acid) | Comparative test4 (ursolic acid potassium salt) | Comparative test 5 (solid dispersion of ursolic acid with phospholipids) |
| Ursolic acid in solution (mg/ml) | 1.165 | 1.082 | 0.032 | 0.154 | 0.436 |

| | FeSSIF pH = 5.0 | | | | |
|---|---|---|---|---|---|
| | Solid dispersion of ursolic acid potassium salt with phospholipids | Test 2 (solid dispersion of ursolic acid potassium salt of example 3 | Ursolic acid | Ursolic acid potassium salt | Comparative test 5 (solid dispersion of ursolic acid with phospholipids) |
| Ursolic acid in solution (mg/ml) | 1.072 | 0.806 | 0.083 | 0.318 | 0.413 |

*limit of detection

The invention claimed is:

1. A solid dispersion comprising a potassium salt of ursolic acid and a phospholipid, wherein the weight ratio between the potassium salt of ursolic acid and the phospholipid ranges from 0.5:1 to 2:1, wherein the phospholipid is soy lecithin or sunflower lecithin.

2. The solid dispersion according to claim 1, wherein the solid dispersion further comprises one or more excipients selected from:

cellulose, cellulose ethers, calcium phosphate, calcium carbonate, mannitol, maltodextrins, isomalt and combinations thereof;

silica, talc, stearic acid, magnesium stearate and combinations thereof;

sucrose esters, polysorbates, polyoxyethylenated castor oil derivatives, D-α-tocopheryl-polyethylene glycol succinate and combinations thereof.

3. The solid dispersion according to claim 2, wherein the weight ratio between the one or more excipient and the potassium salt of ursolic acid ranges from 0.5:1 to 2:1.

4. The solid dispersion according to claim 2, wherein the solid dispersion consists essentially of:

a potassium salt of ursolic acid;

a phospholipid;

cellulose or a cellulose ether or a combination thereof; and silica.

5. The solid dispersion according to claim 4, wherein the solid dispersion consists of a potassium salt of ursolic acid; a phospholipid which is sunflower lecithin; cellulose or a cellulose ether or a combination thereof; and silica.

6. The solid dispersion according to claim 2, which comprises a potassium salt of ursolic acid, a phospholipid which is sunflower lecithin, cellulose and silica.

7. The solid dispersion according to claim 1, having a particle size ranging from 10 μm to 300 μm.

8. A process for the preparation of the solid dispersion according to claim 1, said process comprising:

a-1) suspending the potassium salt of ursolic acid and the phospholipid in an alcohol to provide a suspension, wherein the weight ratio between the potassium salt of ursolic acid and the phospholipid ranges from 0.5:1 to 2:1;

b-1) heating the suspension obtained in step a-1) under reflux for a time ranging from 5 minutes to 5 hours;

c-1) removing the solvent to provide a solid dispersion.

9. A process for the preparation of the solid dispersion according to claim 2, said process comprising:

a-2) suspending the potassium salt of ursolic acid, the phospholipid, and the one or more excipients in an alcohol to provide a suspension, wherein the weight ratio between the potassium salt of ursolic acid and the phospholipid ranges from 0.5:1 to 2:1;

b-2) heating the suspension obtained in step a-2) under reflux for a time ranging from 5 minutes to 5 hours;

c-2) removing the alcohol to obtain a solid, optionally adding a further excipient and grinding to provide a solid dispersion.

10. An oral dosage formulation comprising the solid dispersion according to claim 1, in admixture with further ingredients of pharmaceutical or nutraceutical grade.

11. The process according to claim 8, wherein in step b-1) the suspension obtained in step a-1) is heated under reflux for a time ranging from 1 to 3 hours.

12. The process according to claim 9, wherein in step b-2) the suspension obtained in step a-2) is heated under reflux for a time ranging from 1 to 3 hours.

* * * * *